(12) United States Patent
Roy et al.

(10) Patent No.: US 10,806,505 B2
(45) Date of Patent: *Oct. 20, 2020

(54) VESSEL SEALING INSTRUMENT

(71) Applicant: Covidien LP, Mansfield, MA (US)

(72) Inventors: Jeffrey M. Roy, Boulder, CO (US); Mark J. Huseman, Broomfield, CO (US); Ryan C. Artale, Crested Butte, CO (US); Roy Goodwin, Oroville, CA (US); David Galbraith, Orville, CA (US)

(73) Assignee: COVIDIEN LP, Mansfield, MA (US)

( * ) Notice: Subject to any disclaimer, the term of this patent is extended or adjusted under 35 U.S.C. 154(b) by 169 days.

This patent is subject to a terminal disclaimer.

(21) Appl. No.: 15/970,673

(22) Filed: May 3, 2018

(65) Prior Publication Data

US 2018/0250064 A1   Sep. 6, 2018

Related U.S. Application Data

(63) Continuation of application No. 14/636,276, filed on Mar. 3, 2015, now Pat. No. 9,974,600, which is a continuation of application No. 12/895,020, filed on Sep. 30, 2010, now Pat. No. 9,005,200.

(51) Int. Cl.
*A61B 18/14* (2006.01)
*A61B 18/00* (2006.01)

(52) U.S. Cl.
CPC ...... *A61B 18/1442* (2013.01); *A61B 18/1445* (2013.01); *A61B 2018/0063* (2013.01); *A61B 2018/1455* (2013.01); *Y10T 29/49174* (2015.01)

(58) Field of Classification Search
CPC ............ A61B 18/1442; A61B 18/1445; A61B 2018/1455; A61B 2018/0063; Y10T 29/49174

See application file for complete search history.

(56) References Cited

U.S. PATENT DOCUMENTS

| D249,549 S | 9/1978 | Pike |
| D263,020 S | 2/1982 | Rau, III |
| 4,435,856 A | 3/1984 | L'Esperance |

(Continued)

FOREIGN PATENT DOCUMENTS

| CN | 101507635 A | 8/2009 |
| DE | 2415263 A1 | 10/1975 |

(Continued)

OTHER PUBLICATIONS

Int'l Search Report EP 98944778.4 dated Oct. 31, 2000.

(Continued)

*Primary Examiner* — Catherine M Voorhees

(57) ABSTRACT

A bipolar electrosurgical instrument is provided. The bipolar electrosurgical instrument includes first and second shafts each having a jaw member extending from a distal end thereof and a handle disposed at a proximal end thereof for effecting movement of the jaw members relative to one another. A first conductive lead is adapted to connect to a first electrical potential and a second conductive lead is adapted to connect to a second electrical potential. One of the first and second conductive leads extends through the pivot to connect to a respective jaw member.

20 Claims, 3 Drawing Sheets

(56) References Cited

U.S. PATENT DOCUMENTS

| | | | |
|---|---|---|---|
| D295,893 S | 5/1988 | Sharkany et al. | |
| D295,894 S | 5/1988 | Sharkany et al. | |
| D298,353 S | 11/1988 | Manno | |
| D299,413 S | 1/1989 | DeCarolis | |
| 5,211,655 A | 5/1993 | Hasson | |
| D343,453 S | 1/1994 | Noda | |
| D348,930 S | 7/1994 | Olson | |
| D349,341 S | 8/1994 | Lichtman et al. | |
| 5,342,359 A | 8/1994 | Rydell | |
| D354,564 S | 1/1995 | Medema | |
| D358,887 S | 5/1995 | Feinberg | |
| D384,413 S | 9/1997 | Zlock et al. | |
| 5,669,885 A | 9/1997 | Smith | |
| 5,797,927 A | 8/1998 | Yoon | |
| 5,797,958 A | 8/1998 | Yoon | |
| D402,028 S | 12/1998 | Grimm et al. | |
| 5,922,002 A * | 7/1999 | Yoon | A61B 17/12013 606/139 |
| D416,089 S | 11/1999 | Barton et al. | |
| 5,984,939 A | 11/1999 | Yoon | |
| D424,694 S | 5/2000 | Tetzlaff et al. | |
| D425,201 S | 5/2000 | Tetzlaff et al. | |
| 6,063,086 A | 5/2000 | Benecke et al. | |
| 6,105,256 A | 8/2000 | Budrow | |
| 6,206,877 B1 | 3/2001 | Kese et al. | |
| D449,886 S | 10/2001 | Tetzlaff et al. | |
| 6,324,712 B1 | 12/2001 | Elsener, Sr. | |
| 6,334,861 B1 | 1/2002 | Chandler et al. | |
| D454,951 S | 3/2002 | Bon | |
| D457,958 S | 5/2002 | Dycus et al. | |
| D457,959 S | 5/2002 | Tetzlaff et al. | |
| D465,281 S | 11/2002 | Lang | |
| D466,209 S | 11/2002 | Bon | |
| D493,888 S | 8/2004 | Reschke | |
| D496,997 S | 10/2004 | Dycus et al. | |
| D499,181 S | 11/2004 | Dycus et al. | |
| 6,840,938 B1 | 1/2005 | Morley et al. | |
| D502,994 S | 3/2005 | Blake, III | |
| 6,887,240 B1 | 5/2005 | Lands et al. | |
| D509,297 S | 9/2005 | Wells | |
| D525,361 S | 7/2006 | Hushka | |
| 7,101,371 B2 | 9/2006 | Dycus et al. | |
| 7,101,372 B2 | 9/2006 | Dycus et al. | |
| 7,101,373 B2 | 9/2006 | Dycus et al. | |
| D531,311 S | 10/2006 | Guerra et al. | |
| 7,118,587 B2 | 10/2006 | Dycus et al. | |
| 7,131,971 B2 | 11/2006 | Dycus et al. | |
| D533,274 S | 12/2006 | Visconti et al. | |
| D533,942 S | 12/2006 | Kerr et al. | |
| D535,027 S | 1/2007 | James et al. | |
| D538,932 S | 3/2007 | Malik | |
| D541,418 S | 4/2007 | Schechter et al. | |
| D541,611 S | 5/2007 | Aglassinger | |
| D541,938 S | 5/2007 | Kerr et al. | |
| D545,432 S | 6/2007 | Watanabe | |
| D547,154 S | 7/2007 | Lee | |
| 7,244,257 B2 | 7/2007 | Podhajsky et al. | |
| 7,255,697 B2 | 8/2007 | Dycus et al. | |
| 7,267,677 B2 * | 9/2007 | Johnson | A61B 18/1445 606/171 |
| 7,329,256 B2 | 2/2008 | Johnson et al. | |
| D564,662 S | 3/2008 | Moses et al. | |
| D567,943 S | 4/2008 | Moses et al. | |
| 7,384,420 B2 | 6/2008 | Dycus et al. | |
| D575,395 S | 8/2008 | Hushka | |
| D575,401 S | 8/2008 | Hixson et al. | |
| D582,038 S | 12/2008 | Swoyer et al. | |
| 7,510,556 B2 | 3/2009 | Nguyen et al. | |
| 7,513,898 B2 | 4/2009 | Johnson et al. | |
| 7,722,607 B2 | 5/2010 | Dumbauld et al. | |
| D617,900 S | 6/2010 | Kingsley et al. | |
| D617,901 S | 6/2010 | Unger et al. | |
| D617,902 S | 6/2010 | Twomey et al. | |
| D617,903 S | 6/2010 | Unger et al. | |
| D618,798 S | 6/2010 | Olson et al. | |
| D621,503 S | 8/2010 | Otten et al. | |
| 7,766,910 B2 | 8/2010 | Hixson et al. | |
| 7,887,536 B2 | 2/2011 | Johnson et al. | |
| 7,896,878 B2 | 3/2011 | Johnson et al. | |
| 8,070,748 B2 | 12/2011 | Hixson et al. | |
| 8,092,451 B2 | 1/2012 | Schechter et al. | |
| 8,133,254 B2 | 3/2012 | Dumbauld et al. | |
| 8,162,965 B2 | 4/2012 | Reschke et al. | |
| 8,187,273 B2 | 5/2012 | Kerr et al. | |
| 8,215,182 B2 | 7/2012 | Artale et al. | |
| 8,257,352 B2 | 9/2012 | Lawes et al. | |
| 8,266,783 B2 | 9/2012 | Brandt et al. | |
| 8,277,446 B2 | 10/2012 | Heard | |
| 8,287,536 B2 | 10/2012 | Mueller et al. | |
| 8,292,067 B2 | 10/2012 | Chowaniec et al. | |
| 8,292,886 B2 | 10/2012 | Kerr et al. | |
| 8,298,232 B2 | 10/2012 | Unger | |
| 8,298,233 B2 | 10/2012 | Mueller | |
| 8,323,310 B2 | 12/2012 | Kingsley | |
| 8,328,802 B2 | 12/2012 | Deville et al. | |
| 8,343,150 B2 | 1/2013 | Artale | |
| 8,343,151 B2 | 1/2013 | Siebrecht et al. | |
| 8,348,948 B2 | 1/2013 | Bahney | |
| 8,357,159 B2 | 1/2013 | Romero | |
| 8,388,647 B2 | 3/2013 | Nau, Jr. et al. | |
| 8,409,246 B2 | 4/2013 | Kerr et al. | |
| 8,409,247 B2 | 4/2013 | Garrison et al. | |
| 8,425,511 B2 | 4/2013 | Olson | |
| 8,430,876 B2 | 4/2013 | Kappus et al. | |
| 8,430,877 B2 | 4/2013 | Kerr et al. | |
| 8,439,911 B2 | 5/2013 | Mueller | |
| 8,439,913 B2 | 5/2013 | Horner et al. | |
| 8,469,991 B2 | 6/2013 | Kerr | |
| 8,469,992 B2 | 6/2013 | Roy et al. | |
| 8,480,671 B2 | 7/2013 | Mueller | |
| 8,491,624 B2 | 7/2013 | Kerr et al. | |
| 8,491,625 B2 | 7/2013 | Horner | |
| 8,491,626 B2 | 7/2013 | Roy et al. | |
| 8,512,336 B2 | 8/2013 | Couture | |
| 8,512,371 B2 | 8/2013 | Kerr et al. | |
| 8,641,712 B2 | 2/2014 | Couture | |
| 8,641,713 B2 | 2/2014 | Johnson et al. | |
| 8,652,135 B2 | 2/2014 | Nau, Jr. | |
| 8,663,222 B2 | 3/2014 | Anderson et al. | |
| 8,814,864 B2 | 8/2014 | Gilbert | |
| 8,926,610 B2 | 1/2015 | Hafner et al. | |
| 9,005,200 B2 * | 4/2015 | Roy | A61B 18/1442 606/52 |
| 9,974,600 B2 * | 5/2018 | Roy | A61B 18/1442 |
| 2004/0082952 A1 | 4/2004 | Dycus et al. | |
| 2004/0087940 A1 | 5/2004 | Jahns et al. | |
| 2004/0116924 A1 | 6/2004 | Dycus et al. | |
| 2004/0193153 A1 | 9/2004 | Sartor et al. | |
| 2005/0101952 A1 | 5/2005 | Lands et al. | |
| 2005/0113826 A1 * | 5/2005 | Johnson | A61B 18/1442 606/45 |
| 2005/0154387 A1 | 7/2005 | Moses et al. | |
| 2006/0041254 A1 | 2/2006 | Francischelli et al. | |
| 2006/0079933 A1 | 4/2006 | Hushka et al. | |
| 2006/0190035 A1 | 8/2006 | Hushka et al. | |
| 2006/0217706 A1 | 9/2006 | Lau et al. | |
| 2006/0259036 A1 | 11/2006 | Tetzlaff et al. | |
| 2008/0215048 A1 | 9/2008 | Hafner et al. | |
| 2009/0012520 A1 | 1/2009 | Hixson et al. | |
| 2009/0125026 A1 | 5/2009 | Rioux et al. | |
| 2009/0182330 A1 | 7/2009 | D'Amelio et al. | |
| 2009/0182331 A1 * | 7/2009 | D'Amelio | A61B 18/1442 606/51 |
| 2010/0280511 A1 | 11/2010 | Rachlin et al. | |
| 2010/0331839 A1 | 12/2010 | Schechter et al. | |
| 2011/0034918 A1 | 2/2011 | Reschke | |
| 2011/0046623 A1 | 2/2011 | Reschke | |
| 2011/0054468 A1 | 3/2011 | Dycus | |
| 2011/0054471 A1 | 3/2011 | Gerhardt et al. | |
| 2011/0060334 A1 | 3/2011 | Brandt et al. | |
| 2011/0060335 A1 | 3/2011 | Harper et al. | |
| 2011/0071523 A1 | 3/2011 | Dickhans | |
| 2011/0073246 A1 | 3/2011 | Brandt et al. | |
| 2011/0073594 A1 | 3/2011 | Bonn | |

(56) References Cited

U.S. PATENT DOCUMENTS

| | | |
|---|---|---|
| 2011/0077648 A1 | 3/2011 | Lee et al. |
| 2011/0118736 A1 | 5/2011 | Harper et al. |
| 2011/0190653 A1 | 8/2011 | Harper et al. |
| 2011/0190765 A1 | 8/2011 | Chojin |
| 2011/0193608 A1 | 8/2011 | Krapohl |
| 2011/0218530 A1 | 9/2011 | Reschke |
| 2011/0230880 A1 | 9/2011 | Chojin et al. |
| 2011/0251605 A1 | 10/2011 | Hoarau et al. |
| 2011/0251606 A1 | 10/2011 | Kerr |
| 2011/0251611 A1 | 10/2011 | Horner et al. |
| 2011/0270245 A1 | 11/2011 | Horner et al. |
| 2011/0270250 A1 | 11/2011 | Horner et al. |
| 2011/0270251 A1 | 11/2011 | Horner et al. |
| 2011/0276048 A1 | 11/2011 | Kerr et al. |
| 2011/0276049 A1 | 11/2011 | Gerhardt |
| 2011/0295251 A1 | 12/2011 | Garrison |
| 2011/0295313 A1 | 12/2011 | Kerr |
| 2011/0301600 A1 | 12/2011 | Garrison et al. |
| 2011/0301604 A1 | 12/2011 | Horner et al. |
| 2011/0319886 A1 | 12/2011 | Chojin et al. |
| 2011/0319888 A1 | 12/2011 | Mueller et al. |
| 2012/0022532 A1 | 1/2012 | Garrison |
| 2012/0041438 A1 | 2/2012 | Nau, Jr. et al. |
| 2012/0059372 A1 | 3/2012 | Johnson |
| 2012/0059374 A1 | 3/2012 | Johnson et al. |
| 2012/0059375 A1 | 3/2012 | Couture et al. |
| 2012/0059408 A1 | 3/2012 | Mueller |
| 2012/0059409 A1 | 3/2012 | Reschke et al. |
| 2012/0083785 A1 | 4/2012 | Roy et al. |
| 2012/0083786 A1 | 4/2012 | Artale et al. |
| 2012/0083827 A1 | 4/2012 | Artale et al. |
| 2012/0172873 A1 | 7/2012 | Artale et al. |

FOREIGN PATENT DOCUMENTS

| | | |
|---|---|---|
| DE | 02514501 A1 | 10/1976 |
| DE | 2627679 A1 | 1/1977 |
| DE | 03423356 C2 | 6/1986 |
| DE | 03612646 A1 | 4/1987 |
| DE | 8712328 U1 | 2/1988 |
| DE | 04303882 C2 | 2/1995 |
| DE | 04403252 A1 | 8/1995 |
| DE | 19515914 C1 | 7/1996 |
| DE | 19506363 A1 | 8/1996 |
| DE | 29616210 U1 | 11/1996 |
| DE | 19608716 C1 | 4/1997 |
| DE | 19751106 A1 | 5/1998 |
| DE | 19738457 A1 | 3/1999 |
| DE | 19751108 A1 | 5/1999 |
| DE | 10045375 A1 | 4/2002 |
| DE | 102004026179 A1 | 12/2005 |
| DE | 202007009317 U1 | 10/2007 |
| EP | 0589555 A1 | 3/1994 |
| EP | 1159926 A2 | 3/2003 |
| EP | 1532932 A1 | 5/2005 |
| EP | 1609430 A1 | 12/2005 |
| JP | 61501068 | 9/1984 |
| JP | 55106 | 1/1993 |
| JP | 0540112 | 2/1993 |
| JP | 65502328 | 3/1994 |
| JP | 06343644 A | 12/1994 |
| JP | 07265328 A | 10/1995 |
| JP | 08056955 | 3/1996 |
| JP | 08252263 A | 10/1996 |
| JP | 09010223 | 1/1997 |
| JP | 1024051 | 1/1998 |
| JP | 11070124 | 3/1999 |
| JP | 11169381 | 6/1999 |
| JP | 11244298 A | 9/1999 |
| JP | 2000102545 A | 4/2000 |
| JP | 2000342599 A | 12/2000 |
| JP | 2000350732 A2 | 12/2000 |
| JP | 2001008944 | 1/2001 |
| JP | 2001029356 | 2/2001 |
| JP | 2001128990 A | 5/2001 |
| JP | 2004526513 A | 9/2004 |
| JP | 2005144193 A | 6/2005 |
| SU | 401367 A1 | 10/1973 |
| WO | 0036986 A1 | 6/2000 |
| WO | 0154604 A1 | 8/2001 |
| WO | 2005004734 A1 | 1/2005 |
| WO | 2005110264 A2 | 4/2006 |
| WO | 2009003575 A1 | 1/2009 |

OTHER PUBLICATIONS

Int'l Search Report EP 98957771 dated Aug. 9, 2001.
Int'l Search Report EP 98957773 dated Aug. 1, 2001.
Int'l Search Report EP 98958575.7 dated Sep. 20, 2002.
Int'l Search Report EP 04013772.1 dated Apr. 1, 2005.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 08 020807.7 dated Apr. 24, 2009.
Int'l Search Report EP 09 003677.3 dated May 4, 2009.
Int'l Search Report EP 09 003813.4 dated Aug. 3, 2009.
Int'l Search Report EP 09 004491.8 dated Sep. 9, 2009.
Int'l Search Report EP 09 005051.9 dated Jul. 6, 2009.
Int'l Search Report EP 09 005575.7 dated Sep. 9, 2009.
Int'l Search Report EP 09 010521.4 dated Dec. 16, 2009.
Int'l Search Report EP 09 011745.8 dated Jan. 5, 2010.
Int'l Search Report EP 09 012629.3 dated Dec. 8, 2009.
Int'l Search Report EP 09 012687.1 dated Dec. 23, 2009.
Int'l Search Report EP 09 012688.9 dated Dec. 28, 2009.
Int'l Search Report EP 09 152267.2 dated Jun. 15, 2009.
Int'l Search Report EP 09 152898.4 dated Jun. 10, 2009.
Int'l Search Report EP 09 154850.3 dated Jul. 20, 2009.
Int'l Search Report EP 09 160476.9 dated Aug. 4, 2009.
Int'l Search Report EP 09 164903.8 dated Aug. 21, 2009.
Int'l Search Report EP 09 165753.6 dated Nov. 11, 2009.
Int'l Search Report EP 09 168153.6 dated Jan. 14, 2010.
Int'l Search Report EP 09 168810.1 dated Feb. 2, 2010.
Int'l Search Report EP 09 172749.5 dated Dec. 4, 2009.
Int'l Search Report EP 10 000259.1 dated Jun. 30, 2010.
Int'l Search Report EP 10 157500.9 dated Jul. 30, 2010.
Int'l Search Report EP 10 159205.3 dated Jul. 7, 2010.
Int'l Search Report EP 10 160870,1 dated Aug. 9, 2010.
Int'l Search Report EP 10 161596.1 dated Jul. 28, 2010.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/08146 dated Aug. 8, 2003.
Int'l Search Report PCT/US03/18676 dated Sep. 19, 2003.
Int'l Search Report PCT/US03/28534 dated Dec. 19, 2003.
Int'l Search Report PCT/US04/03436 dated Mar. 3, 2005.
Int'l Search Report PCT/US04/13273 dated Dec. 15, 2004.
Int'l Search Report PCT/US04/15311 dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/52460 dated Apr. 24, 2008.
Int'l Search Report PCT/US08/61498 dated Sep. 22, 2008.
Int'l Search Report PCT/US09/032690 dated Jun. 16, 2009.
Australian Examination Report from Appl. No. 2016201424 dated Apr. 15, 2017.
Japanese Office Action and English language translation issued in Appl. No. JP 2016-075652 dated Apr. 3, 2017.
Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04752343.6 dated Jul. 20, 2007.

(56) References Cited

OTHER PUBLICATIONS

Int'l Search Report EP 05002671.5 dated Dec. 22, 2008.
Int'l Search Report EP 05002674.9 dated Jan. 16, 2009.
Int'l Search Report EP 05013463.4 dated Oct. 7, 2005.
Int'l Search Report EP 05013894 dated Feb. 3, 2006.
Int'l Search Report EP 05013895.7 dated Oct. 21, 2005.
Int'l Search Report EP 05016399.7 dated Jan. 13, 2006.
Int'l Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020532 dated Jan. 10, 2006.
Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 009026.1 dated Oct. 8, 2007.
Int'l Search Report Extended—EP 07 009029.5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.
Int'l Search Report EP 07 015191.5 dated Jan. 23, 2008.
Australian Examination Report corresponding to counterpart application AU 2015204333 dated Sep. 4, 2015.
European Search Report EP13757413 dated Sep. 14, 2015.
Extended European Search Report corresponding to counterpart Int'l Application No. EP 15 17 9958.2 dated Dec. 16, 2015.
European Search Report for European Application No. 11183265.5 dated Nov. 17, 2011.
Australian Examination Report dated Dec. 17, 2014 issued in Australian Appln. No. 2014205809.
Michael Choti, "Abdominoperineal Resection with the LigaSure Vessel Sealing System and LigaSure Atlas 20 cm Open Instrument" Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps", Feb. 6, 1967 (Feb. 6, 1965), British Medical Journal Feb. 6, 1976, vol. 1, nr. 5431 p. 361, ISSN: 0007-1447.
Carbonell et al., "Comparison of the Gyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte,NC; Date: Aug. 2003.
Peterson et al., "Comparison of Healing Process Following Ligation with Sutures and Bipolar Vessel Sealing" Surgical Technology International (2001).
"Electrosurgery: A Historical Overview", Innovations in Electrosurgery; Sales/Product Literature; Dec. 31, 2000.

Johnson et al. "Evaluation of a Bipolar Electrothermal Vessel Sealing Device in Hemorrhoidectomy" Sales/Product Literature; Jan. 2004.
E. David Crawford, "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al. "Extended Left Hemicolectomy Using the LigaSure Vessel Sealing System" Innovations That Work; Sep. 1999.
Kennedy et al. "High-burst-strength, feedback-controlled bipolar vessel sealing" Surgical Endoscopy (1998) 12:876-878.
Burdette et al. "In Vivo Probe Measurement Technique for Determining Dielectric Properties At VHF Through Microwave Frequencies", IEEE Transactions on Microwave Theory and Techniques vol. MTT-28, No. 4, Apr. 1980 pp. 414-427.
Carus et al., "Initial Experience With the LigaSure Vessel Sealing System in Abdominal Surgery" Innovations That Work,Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer"; Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al., "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females". Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room"; Sales/Product Literature 2001.
Bergdahl et al., "Studies on Coagulation and the Development of an Automatic Computerized Bipolar Coagulator" J. Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA , Feb. 2001.
Sayfan et al., "Sutureless Closed Hemorrhoidectomy: A New Technique" Annals of Surgery, vol. 234, No. 1, Jul. 2001, pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.

(56) References Cited

OTHER PUBLICATIONS

Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001)71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery"; Grand Rounds in Urology 1999 vol. 1 Issue 4 pp. 10-17.
Craig Johnson, "Use of the LigaSure Vessel Sealing System in Bloodless Hemorrhoidectomy"; Innovations That Work, Mar. 2000.
Levy et al. "Use of a New Energy-based Vessel Ligation Device During Vaginal Hysterectomy"; Int'l Federation of Gynecology and Obstetrics (FIGO) World Congress 1999.
Barbara Levy, "Use of a New Vessel Ligation Device During Vaginal Hysterectomy"; FIGO 2000, Washington, D.C.
E. David Crawford, "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy"; Sales/Product Literature 2000.
Crouch et al. "A Velocity-Dependent Model for Needle Insertion in Soft Tissue"; MICCAI 2005; LNCS 3750 pp. 624-632, Dated: 2005.
McLellan et al., "Vessel Sealing for Hemostasis During Pelvic Surgery" Int'l Federation of Gynecology and Obstetrics FIGO World Congress 2000, Washington, DC.
McLellan et al. "Vessel Sealing for Hemostasis During Gynecologic Surgery" Sales/Product Literature 1999.
Int'l Search Report EP 07 015601.3 dated Jan. 4, 2008.
Int'l Search Report EP 07 016911 dated May 28, 2010.
Int'l Search Report EP 07 020283.3 dated Feb. 5, 2008.
Int'l Search Report EP 07 021646.0 dated Mar. 20, 2008.
Int'l Search Report EP 07 021646.0 dated Jul. 9, 2008.
Int'l Search Report EP 07 021647.8 dated May 2, 2008.
Int'l Search Report EP 08 002692.5 dated Dec. 12, 2008.
Canadian Office Action from Appl. No. CA 2,753,712 dated Mar. 24, 2017.
Extended European Search Report dated Aug. 8, 2017 issued in Appl. No. EP 17168924.3 (7 pages).
Notice of Allowance dated Aug. 1, 2017 in Japanese Appl. No. JP 2016-075652 (no English Abstract available).

* cited by examiner

VESSEL SEALING INSTRUMENT

CROSS-REFERENCE TO RELATED APPLICATIONS

This application is a continuation of U.S. patent application Ser. No. 14/636,276 filed on Mar. 3, 2015, which is a continuation of U.S. patent application Ser. No. 12/895,020 filed on Sep. 30, 2010, now U.S. Pat. No. 9,005,200, the entire contents of each of which are incorporated herein by reference.

BACKGROUND

Technical Field

The present disclosure relates to forceps used for open surgical procedures. More particularly, the present disclosure relates to a forceps which applies a combination of mechanical clamping pressure and electrosurgical current to seal tissue.

Description of Related Art

Electrosurgical forceps, e.g., commonly used in open surgical procedures, are configured to grasp, dissect and/or clamp tissue. Electrosurgical forceps is a simple plier-like tool which utilizes both mechanical clamping action and electrical energy to respectively constrict vessels and effect hemostasis by heating the tissue and blood vessels to coagulate, cauterize and/or seal tissue. Electrosurgical forceps may be configured for monopolar or bipolar use. For the purposes herein, the present disclosure is directed to electrosurgical forceps that are configured for bipolar use.

Bipolar electrosurgical forceps (forceps) utilize two generally opposing electrodes that are disposed on the inner opposing surfaces of jaw members associated with the end effector of the forceps and that are both electrically coupled to an electrosurgical generator. Each electrode is charged to a different electric potential and includes a respective seal plate; the seal plates are isolated from each other. Design of the isolated seal plates requires separate and unique wires to enable RF energy for vessel sealing (opposite poles for alternating current). Typically, because of the limited space of the forceps, one of the wires is routed directly to one of the seal plates and the other wire is routed indirectly around, i.e., "looped," about a pivot member that pivotably couples a pair of shafts associated with the forceps. Looping one of the wires around the pivot member may result in the "looped" wire being exposed to the surgical environment when the jaw members are moved, e.g., from an open to clamped position. As can be appreciated, exposing the wire to the surgical environment may result in damage to the wire, which, in turn, may decrease the operative life of the forceps. Moreover, "looping" the wire around the pivot member may increase manufacture costs, i.e., more wire is needed to loop around the pivot member, and may increase manufacture time of the forceps, i.e., more time is needed to loop the wire around the pivot member.

SUMMARY

The present disclosure provides a bipolar electrosurgical instrument for use in open surgery. The bipolar electrosurgical instrument includes first and second shafts each having a jaw member extending from a distal end thereof. A handle is disposed at proximal ends of the shafts for effecting movement of the jaw members relative to one another about an integrally formed bifurcated pivot member that is supported on one of the jaw members. The jaw members are movable relative to one another about the pivot member from a first position wherein the jaw members are disposed in spaced relation relative to one another to a second position wherein the jaw members cooperate to grasp tissue therebetween. A proximal shaft connector operably couples to one of the first and second shafts and is configured to connect the bipolar electrosurgical instrument to a source of electrosurgical energy providing first and second electrical potentials. A first conductive lead is adapted to connect to the first electrical potential and a second conductive lead is adapted to connect to the second electrical potential. One of the first and second conductive leads extends through the pivot to connect to a respective jaw member.

The present disclosure provides a bipolar electrosurgical instrument for use in open surgery. The bipolar electrosurgical instrument includes first and second shafts each having a jaw member extending from a distal end thereof. A handle is disposed at proximal ends of the shafts for effecting movement of the jaw members relative to one another about a pivot member from a first position wherein the jaw members are disposed in spaced relation relative to one another to a second position wherein the jaw members cooperate to grasp tissue therebetween. A first conductive lead is adapted to connect to a first electrical potential and a second conductive lead is adapted to connect to a second electrical potential. One of the first and second conductive leads extends through the pivot to connect to a respective jaw member.

The present disclosure also provides a method for routing electrical leads through a bipolar electrosurgical instrument. The method includes forming first and second shafts with respective handles at proximal ends thereof and an end effector having two pivotably coupled jaw members at distal ends thereof. One of the jaw members includes a pivot member integrally formed thereon. The pivot member is configured to receive one of a first conductive lead and a second conductive lead therethrough. A step of the method includes coupling the first and second leads to one of the first and second shafts and routing each of the first and second conductive leads therethrough. One of the first and second conductive leads is coupled directly to one of the jaw members and one of the first and second conductive leads is routed through the pivot member and to the other jaw member.

BRIEF DESCRIPTION OF THE DRAWING

Various embodiments of the present disclosure are described hereinbelow with references to the drawings, wherein.

DETAILED DESCRIPTION

Detailed embodiments of the present disclosure are disclosed herein; however, the disclosed embodiments are merely examples of the disclosure, which may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure.

Figure 1:
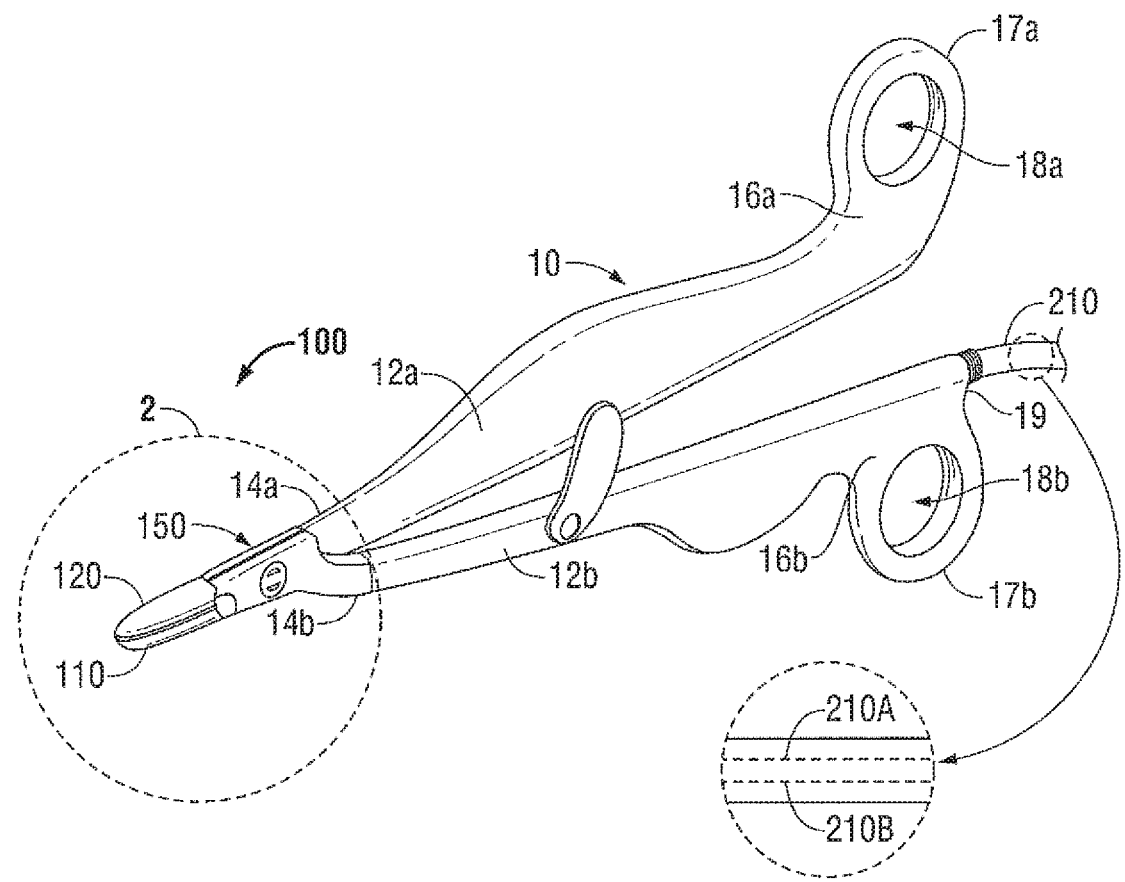
FIG. 1 is a side, perspective view of an open forceps according to an embodiment of the present disclosure.

Referring now to FIGS. 1-6C, and initially with reference to FIG. 1, a forceps 10 for use with open surgical procedures is illustrated. Forceps 10 includes elongated shaft portions 12a and 12b each having a proximal end 16a and 16b, respectively, and a distal end 14a and 14b, respectively. The forceps 10 includes an end effector assembly 100 that attaches to distal ends 14a and 14b of shafts 12a and 12b, respectively. The end effector assembly 100 includes a pair of opposing jaw members 110 and 120 that are pivotably connected about a pivot member 150 (pivot 150).

In the drawings and in the descriptions which follow, the term "proximal", as is traditional, will refer to the end of the forceps 10 which is closer to the user, while the term "distal" will refer to the end which is further from the user.

Shaft 12a includes a handle 17a and shaft 12b includes handle 17b. Finger holes 18a and 18b are respectively disposed at the proximal ends 16a and 16b for receiving a finger of the user. As can be appreciated, finger holes 18a and 18b facilitate movement of the shafts 12a and 12b relative to one another which, in turn, pivot the jaw members 110 and 120 from an open position (FIGS. 6A and 6B) wherein the jaw members 110 and 120 are disposed in spaced relation relative to one another to a clamping or closed position (FIGS. 1, 2, 5 and 6C) wherein the jaw members 110 and 120 cooperate to grasp tissue therebetween.

One of the shafts, e.g., 12b, includes a proximal shaft connector 19 that is designed to connect the forceps 10 to a source of electrosurgical energy such as an electrosurgical generator (not shown). More particularly, proximal shaft connector 19 mechanically cooperates to secure an electrosurgical cable 210 to the forceps 10 such that the user may selectively apply electrosurgical energy as needed. The proximal end of the cable 210 includes a plug (not shown) having a pair of prongs which are configured to electrically and mechanically engage the electrosurgical energy generator. The interior of cable 210 houses a pair of leads 210a and 210b (FIG. 1) which conduct the different electrical potentials from the electrosurgical generator to the jaw members 110 and 120, as explained in greater detail below.

In certain embodiments, a ratchet (not shown) may be operably coupled to the forceps 10 for selectively locking the jaw members 110 and 120 relative to one another at various positions during pivoting.

For a more detailed description of the forceps 10 including the ratchet, end effector 100 including jaw members 110 and 120 (and operative components associated therewith), and electrosurgical cable 210 (including line-feed configurations and/or connections), reference is made to commonly owned U.S. Pat. No. 7,329,256 to Johnson et al., filed on Dec. 23, 2005.

Figure 2:
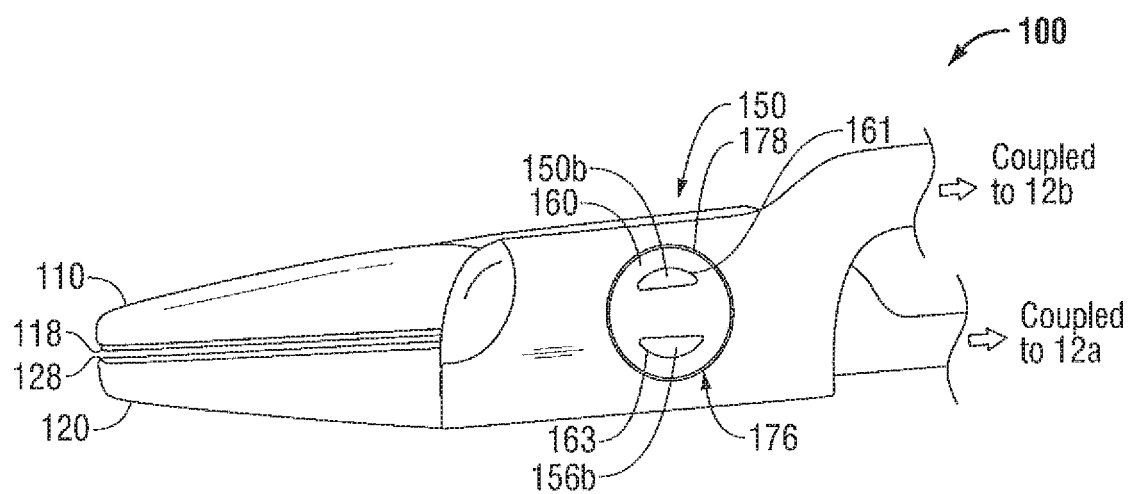
FIG. 2 is a enlarged view of the indicated area of detail in FIG. 1 showing an end effector assembly of the open forceps depicted in FIG. 1.

Referring now to FIG. 2, an enlarged view of the end effector 100 is shown. End effector 100 includes opposing jaw members 110 and 120 that are pivotably coupled to each other via the pivot 150 that is integrally formed with one of the jaw members, e.g., jaw member 110. Jaw members 110 and 120 including pivot 150 are configured such that the leads 210a and 210b connect to the respective jaw members 110 and 120 without the need to "loop" one or both of the leads 210a and 210b around the pivot 150 such that exposure of the leads 210a and 210b to the surgical environment is minimized, if not completely eliminated. In the illustrated embodiment, jaw member 110 is supported on shaft 12a at distal end 14a thereof and jaw member 120 is supported on shaft 12b at a distal end 14b thereof (FIG. 1).

Figure 3:
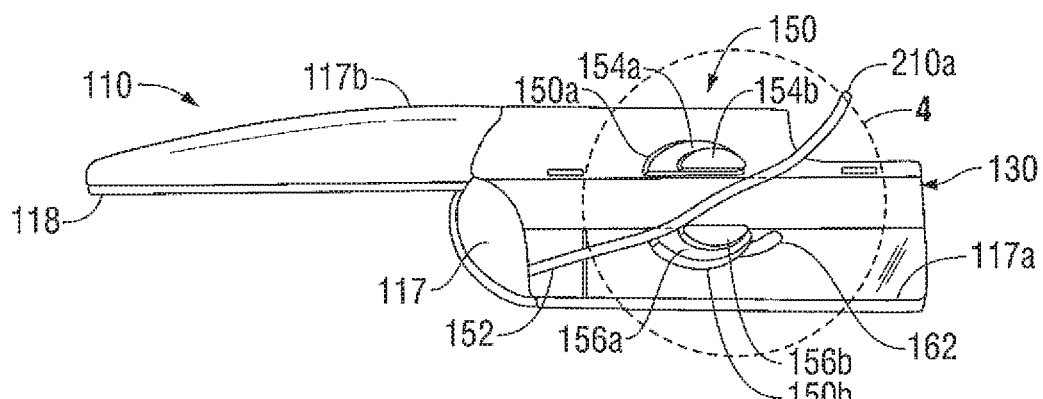
FIG. 3 is an internal, side view of a jaw member associated with the end effector assembly depicted in FIG. 2 showing the inner-working components thereof.

Referring to FIG. 3, jaw member 110 is shown in unassembled and detached from jaw member 120. Jaw member 110 includes a jaw housing 117 having proximal and distal ends 117a and 117b. Distal end 117b is configured to support a seal plate 118 that is isolated from the rest of the jaw housing 117. Proximal end 117a is configured to support the pivot 150. In the illustrated embodiment, the proximal end 117a is elongated with a generally rectangular configuration that may include an arcuate or curved proximal portion (not shown).

In the embodiment illustrated in the representative figures a generally longitudinal channel 130 of suitable dimensions extends substantially along a length of the proximal end 117a (as best seen in FIG. 3). The channel 130 is configured to receive a cutting element or the like, e.g., a knife blade (not shown). More particularly, the channel 130 is configured such that the cutting element may be translated therethrough for cutting or severing tissue that has been electrosurgically or otherwise treated. The channel 130 is also configured to align the cutting element with a longitudinal knife channel that is operably disposed on one or both of the jaw members 110 and 120. For purposes herein, it may be assumed that the longitudinal knife channel is operably disposed on both the jaw members 110 and 120. The depth of the channel 130 is of such dimensions that the lead 210a does not impede and/or contact the knife blade when the knife blade is translated through the channel 130 and the longitudinal knife channel on the jaw members 110 and 120. To this end, an area "A" (FIG. 4) is defined between a pair of sidewalls 130a and 130b that defines the channel 130.

As can be appreciated, in the instance where the forceps 10 is not configured to cut or sever tissue, the jaw member 110 may be configured without the slot 130; this of course will depend on the contemplated uses of a manufacturer, a specific surgical procedure, etc.

Figure 4:
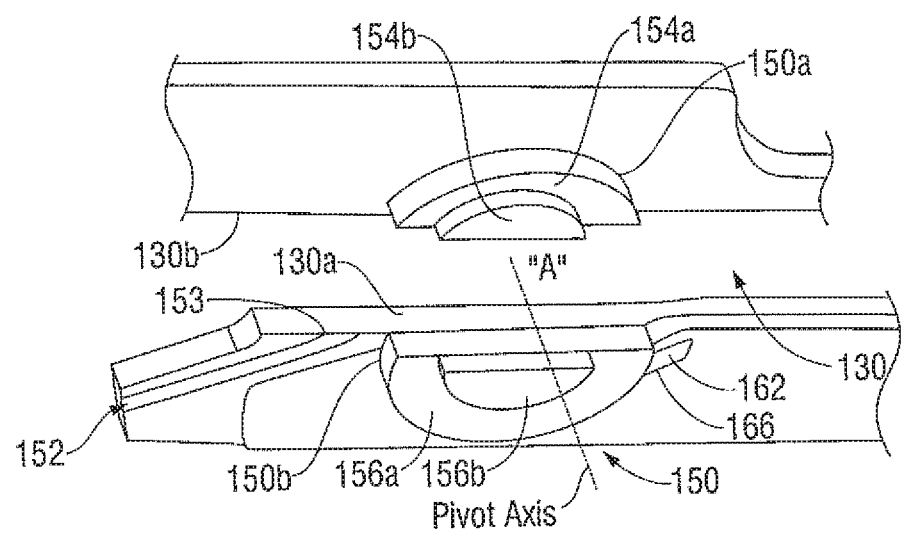
FIG. 4 is a enlarged view of the indicated area of detail in FIG. 3 showing a pivot member associated with the open forceps depicted in FIG. 1.
Figure 5:
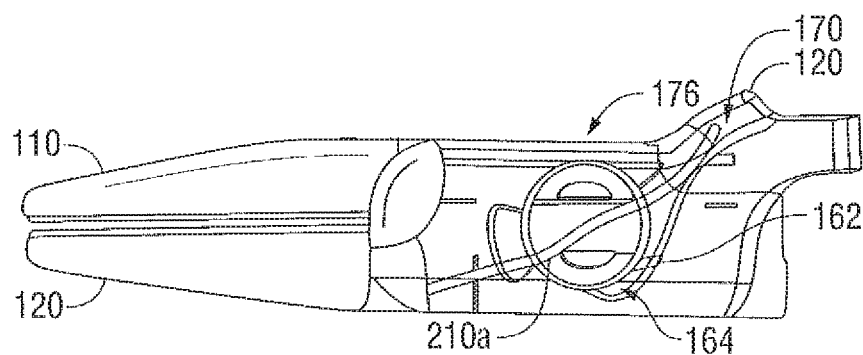
FIG. 5 is a side view of the jaw members with one of the jaw members shown in phantom illustrating a wire routed through the pivot member of FIG. 4.

Referring now to FIG. 4, a wire or lead guide slot 152 is suitably proportioned and operably disposed on the proximal end 117a of the jaw housing 110. The lead guide slot 152 includes a generally elongated configuration and is configured to house the lead 210a and provide a mechanical interface or "pathway" between the lead 210a and seal plate 118. Lead 210a may be secured within the lead guide slot 152 via one or more suitable securement methods, e.g., press-fit, adhesive, etc. In the illustrated embodiment, the lead 210a is press-fit in the lead guide slot 152 and, subsequently, overmolded thereto such that the distal end of lead 210a is in electrical communication with the seal plate 118, as best seen in FIGS. 3 and 5. The distal end of the lead 210a may be secured to seal plate 118 via any suitable method, such as crimping, soldering, etc. Securing lead 210a in this manner facilitates maintaining the lead 210a in a relatively fixed position while also allowing the lead 210a to "flex" or "bend" when the jaw members 110 and 120 are moved from the open to the clamped position, and vice versa (see FIGS. 6A-6C). In the illustrated embodiment, the lead guide slot 152 is oriented at an angle with respect to the longitudinal channel 130, see FIGS. 3 and 4. Disposing the lead guide slot 152 at an angle with respect to the longitudinal channel 130 relieves the stress on the lead 210*a* when the jaw members 110 and 120 are moved from the open to the clamped position, and vice versa.

To facilitate placement and/or securement of the lead 210*a* within the lead guide slot 152, a proximal end 153 of the lead guide slot 152 is operably disposed in close proximity to the pivot 150 and adjacent the channel 130, as best seen in FIG. 4. The proximal end 153 of the lead guide slot 152 does not breach the area "A" defined by the pair of sidewalls 130*a* and 130*b* of the channel 130; this facilitates keeping the knife blade and the lead 210*a* from contacting each other during translation of knife blade through the channel 130.

With reference again to FIGS. 3 and 4, pivot 150 is bifurcated including a pair of spaced-apart members 150*a* and 150*b*. Members 150*a* and 150*b* are operably disposed on each side of the longitudinal channel 130, see FIG. 3. In the illustrated embodiment, the members 150*a* and 150*b* are spaced-apart from each other at a distance that is at least as equal to a width of the longitudinal channel 130; this facilitates translation of the knife blade therethrough.

Each of members 150*a* and 150*b* includes a generally half-cylindrical or semi-cylindrical configuration that together form a split cylindrical configuration configured for engagement with a corresponding aperture 176 on the jaw member 120, to be described in greater detail below. More particularly, member 150*a* includes a stepped configuration having a base portion 154*a* for supporting an extension 154*b* thereon (FIGS. 3 and 4) that is configured to engage a pivot plate 160 operably disposed on the jaw member 120. Likewise, member 150*b* includes a stepped configuration having a base portion 156*a* for supporting an extension 156*b* thereon (FIGS. 3 and 4) that is configured to engage pivot plate 160 operably disposed on the jaw member 120.

Figure 6A:
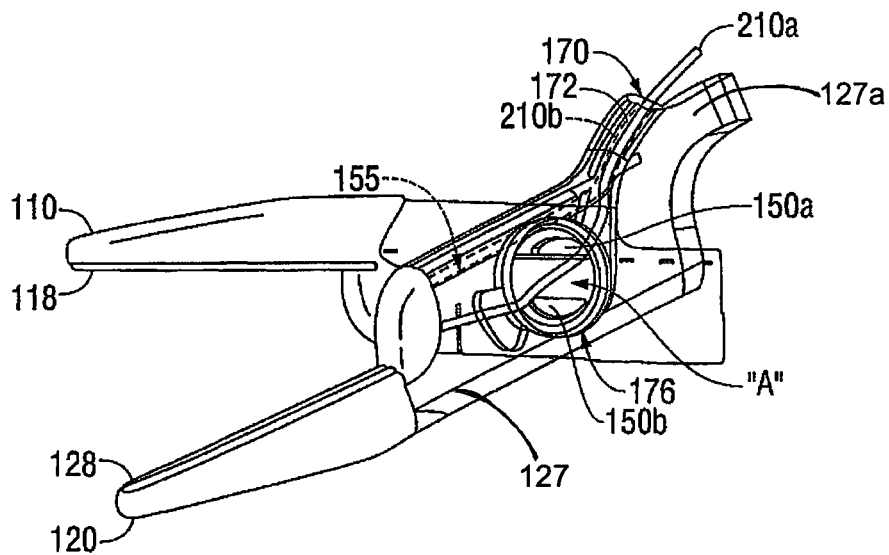
FIGS. 6A-6C are perspective views illustrating the jaw members in various positions.
Figure 6B:
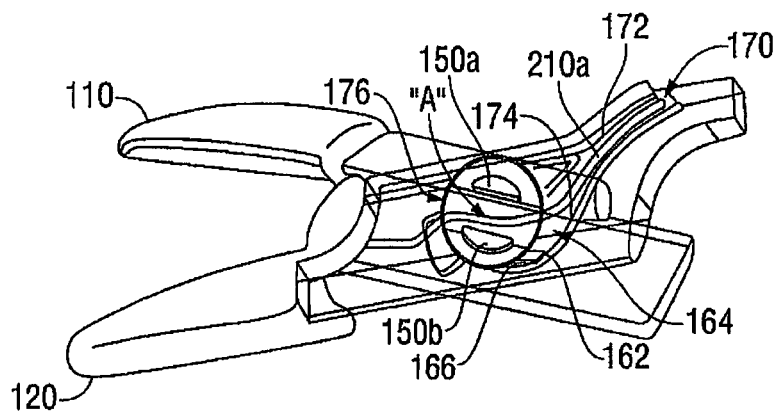
Figure 6C:
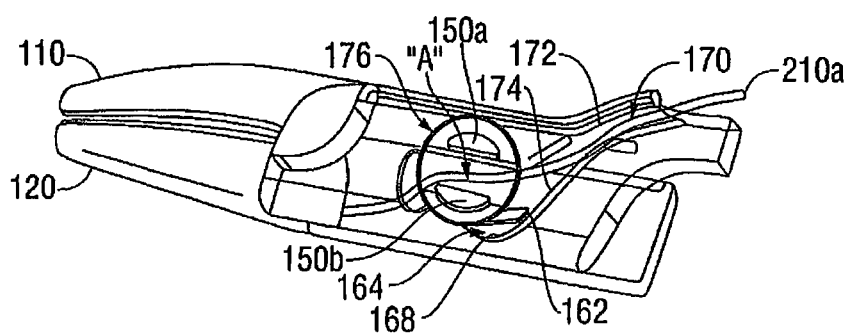

One or more jaw aperture stops 162 (one jaw aperture stop 162 ("stop 162") is illustrated in the representative drawings) of suitable proportion are associated with the pivot 150 (FIGS. 3, 4, 6B and 6C). The stop 162 is configured to limit movement of the jaw members 110 and 120 to a predetermined point when the jaw members 110 and 120 are moved to the open position. With this purpose in mind, stop 162 is operably disposed adjacent one of the two spaced-apart members 150*a* and 150*b*. For illustrative purposes, the stop 162 is shown disposed adjacent spaced-apart member 150*b*. Stop 162 may include any suitable shape and is configured to slidably reside within a corresponding groove 164 disposed on the jaw member 120 (FIGS. 5 and 6C). Stop 162 includes a generally arcuate or curved proximal end, edge or sidewall 166 (FIGS. 4 and 6B) that is contoured to match a corresponding arcuate or curved end, edge or sidewall 168 that partially defines the groove 164 (as best seen in FIG. 6C). Matching the contours of the sidewalls 166 and 168 facilitates rotating the jaw members 110 and 120 from the open to closed positions. When the jaw members 110 and 120 have moved a predetermined distance, the sidewall 166 of the stop 162 contacts the sidewall 168 of the groove 164 and prevents further movement of the jaw members 110 and 120 away from each other (see FIG. 6B in combination with FIG. 6C); this increases the operational life expectancy of the lead 210*a* and, thus, the operational life expectancy of the forceps 10.

Referring to FIGS. 5 and 6A-6C, jaw member 120 is illustrated in phantom. Jaw member 120 and jaw member 110 are substantially identical to one another. In view thereof, only those features unique to jaw member 120 are described herein.

A wire or lead guide slot 155 is suitably proportioned and operably disposed on the proximal end 127*a* of the jaw housing 120 (shown in phantom in FIG. 6A). The lead guide slot 155 provides a mechanical interface or "pathway" between the lead 210*b* and the seal plate 128. Lead 210*b* may be secured within the lead guide slot 155 and to the jaw housing 127 via one or more of the aforementioned securement methods, e.g., press-fit, adhesive, etc. In the illustrated embodiment, the lead 210*b* is press-fit in the lead guide slot 155, the distal end crimped or soldered to the jaw housing 127 adjacent the seal plate 128 and, subsequently, overmolded thereto such that the lead 210*b* is in electrical communication with the seal plate 128. A proximal end of the lead guide slot 155 opens into a raceway 170 (FIGS. 6A-6C).

Raceway 170 is operably disposed at the proximal end 127*a* of the jaw housing 127 and includes a generally elongated configuration with a narrowed proximal end 172 and broadened distal end 174. The raceway 170 provides a path or a point of egress for the leads 210*a* and 210*b* from the shaft 12*b* into the jaw housings 117 and 127.

Proximal end 172 of the raceway is configured such that when the leads 210*a* and 210*b* are positioned therein, the leads 210*a* and 210*b* remain in a substantially fixed orientation, i.e., the leads 210*a* and 210*b* are "press fit" into the proximal end 172 of the raceway.

In certain embodiments, it may prove useful to fixedly secure the leads 210*a* and 210*b* within the proximal end 172 of the raceway 170.

Distal end 174 of the raceway 170 opens into the groove 164 defined by the arcuate or curved sidewall 168 (FIGS. 6B and 6C). Moreover, the distal end 174 of the raceway 170 opens into the area "A" defined between the two spaced-apart members 150*a* and 150*b*, see FIGS. 4 and 6A-6C, for example. This facilitates routing the lead 210*a* through the raceway 170 and between the two spaced-apart members 150*a* and 150*b*, such that the lead 210*a* may be ultimately secured within the lead guide slot 152, see FIG. 3.

A generally circumferential opening 176 of suitable proportion is operably disposed on the jaw member 120 (FIGS. 2 and 6A-6C). The opening 176 is configured to receive the pivot 150 including the two spaced-apart members 150*a* and 150*b* such that the pivot 150 including the two spaced-apart members 150*a* and 150*b* are rotatably movable thereabout.

A circumferential groove 178 of suitable proportion is operably disposed within the opening 176 and is configured to accommodate rotatable movement of the pivot plate 160 (FIG. 2). To this end, the groove 178 includes a circumferential lip or flange (not explicitly shown) that is configured to provide a seat for the pivot plate 160.

Pivot plate 160 is seated on the circumferential flange of the groove 178 and within the opening 176. Pivot plate 160 includes two half cylindrical openings 161 and 163. Openings 161 and 163 are configured to couple to respective spaced-apart members 150*a* and 150*b*, as best seen in FIG. 2. Openings 161 and 163 may couple to the respective spaced-apart members 150*a* and 150*b* via one or more suitable coupling methods, e.g., solder joint, braze joint, weld joint, adhesive, press-fit, friction-fit, etc. In the illustrated embodiment, the openings 161 and 163 are coupled to the respective spaced-apart members 150*a* and 150*b* via a spot weld.

In an assembled configuration, the forceps 10 is utilized in a manner that is conventional in the relevant arts. More particularly, an operator grasps the forceps 10, moves the jaw members 110 and 120 to the open position, positions tissue between the jaw members 110 and 120, clamps down on the tissue therebetween and treats the tissue, e.g., seals the tissue. In certain instances, a knife blade is, subsequently, translated through the jaw members 110 and 120. However, unlike conventional forceps, where one or more of the leads 210a and 210b are exposed to the surgical environment when the jaw members 110 and 120 are moved to the open position, use of the forceps 10 with one of the leads, e.g., lead 210a, routed through the pivot 150 does not expose the lead 210a to the surgical environment, see FIGS. 6A-6C, for example. Accordingly, the risk of compromising the integrity of the lead 210a is diminished, if not eliminated.

From the foregoing and with reference to the various figure drawings, those skilled in the art will appreciate that certain modifications can also be made to the present disclosure without departing from the scope of the same. For example, in embodiments, it may prove useful to dispose the stop 162 on the jaw member without the pivot 150 and dispose the corresponding sidewall 168 on the jaw member with the pivot 150.

A method for routing electrical leads 210a and 210b through a bipolar electrosurgical instrument, e.g., forceps 10, is also disclosed. A step of the method includes forming first and second shafts 12a and 12b with respective handles 17a and 17b at proximal ends thereof and an end effector 100 having two pivotably coupled jaw members 110 and 120 at distal ends thereof. One of the jaw members, e.g., jaw member 110, includes a pivot 150 formed integrally thereon. The pivot 150 is configured to receive one of the electrical leads, e.g., electrical lead 210a, therethrough. The method includes coupling the electrical leads 210a and 210b to one of the first and second shafts, e.g., shaft 12b, and routing each of the electrical leads 210a and 210b therethrough. Electrical lead 210b is coupled directly to the jaw member 120 and electrical lead 210a is routed through the pivot 150 and to the jaw member 110.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An electrosurgical instrument, comprising:
   a first jaw member disposed at a distal end of a first shaft and a second jaw member disposed at a distal end of a second shaft;
   a pivot disposed on one of the first or second jaw members, the jaw members movable about the pivot relative to one another;
   a lead guide slot formed in a surface of the second jaw member and disposed in spaced relation to the pivot;
   a raceway continuous with a proximal end of the lead guide slot and formed in the surface of the second jaw member proximal to the pivot, the raceway including a narrowed portion and a broadened portion;
   a longitudinal groove extending through the pivot and configured to receive a knife therethrough for cutting tissue disposed between the jaw members; and
   a first conductive lead adapted to connect to a first electrical potential and a second conductive lead adapted to connect to a second electrical potential, at least one of the first or second conductive leads routed through the narrowed portion of the raceway.

2. The electrosurgical instrument according to claim 1, wherein the narrowed portion of the raceway is configured to maintain at least one of the first or second conductive leads in a relatively fixed position during movement of the jaw members.

3. The electrosurgical instrument according to claim 1, further comprising a jaw aperture stop disposed on one of the first or second jaw members and configured to limit movement of the jaw members relative to one another.

4. The electrosurgical instrument according to claim 3, further comprising a groove defined in one of the first or second jaw members configured to receive the at least one jaw aperture stop therein.

5. The electrosurgical instrument according to claim 1, further comprising a pivot plate configured to couple to the pivot to couple the first jaw member to the second jaw member.

6. The electrosurgical instrument according to claim 5, wherein the pivot plate is disposed within a circumferential groove defined in one of the first or second jaw members, the circumferential groove configured to facilitate rotation of the pivot during movement of the jaw members.

7. The electrosurgical instrument according to claim 1, further comprising a proximal shaft connector operably coupled to one of the first or second shafts and configured to connect at least one of the first or second jaw members to a source of electrosurgical energy.

8. The electrosurgical instrument according to claim 1, wherein the lead guide slot is defined in the second jaw member distal to the pivot.

9. The electrosurgical instrument according to claim 1, wherein the pivot is configured to be received within an aperture defined through the second jaw member.

10. The electrosurgical instrument according to claim 1, wherein the first conductive lead is routed through the narrowed portion of the raceway to connect to the first jaw member, and the second conductive lead is routed through the narrowed portion of the raceway and the lead guide slot to connect to the second jaw member.

11. An end effector for an electrosurgical instrument, comprising:
    first and second jaw members movable relative to one another about a pivot between an open position and a closed position;
    a knife channel defined along a distal portion of at least one of the first or second jaw members; and
    a lead guide slot disposed on one of the first or second jaw members and extending between the pivot and the knife channel, the lead guide slot disposed at an angle relative to a longitudinal axis defined through the pivot to maintain a conductive lead electrically coupled to one of the first or second jaw members in a relatively fixed position during movement of the first and second jaw members.

12. The end effector according to claim 11, further comprising a raceway defined in one of the first or second jaw members proximal to the pivot, the conductive lead routed through the raceway.

13. The end effector according to claim 12, wherein the raceway includes a narrowed portion and a broadened portion, the conductive lead routed through the narrowed portion of the raceway and the lead guide slot to connect to one of the first or second jaw members.

14. The end effector according to claim 11, further comprising a longitudinal groove defined along a proximal portion of one of the first or second jaw members and disposed in alignment with the knife channel.

15. An end effector for an electrosurgical instrument, comprising:

first and second jaw members movable relative to one another about a pivot between an open position and a closed position;

a knife channel defined along a distal portion of at least one of the first or second jaw members, the knife channel configured to receive a knife therethrough; and a longitudinal groove formed in a surface of one of the first or second jaw members proximal to the knife channel and configured to receive the knife therethrough, the longitudinal groove extending through the pivot and disposed in alignment with the knife channel.

16. The end effector according to claim 15, further comprising a lead guide slot disposed on one of the first or second jaw members, the lead guide slot configured to maintain a conductive lead electrically coupled to one of the first or second jaw members in a relatively fixed position during movement of the first and second jaw members.

17. The end effector according to claim 15, wherein a distal end of the longitudinal groove is disposed proximal to a proximal end of the knife channel.

18. The end effector according to claim 15, further comprising a raceway defined in one of the first or second jaw members proximal to the pivot, the raceway including a narrowed portion and a broadened portion.

19. The end effector according to claim 18, wherein the narrowed portion of the raceway is configured to route a conductive lead to one of the first or second jaw members.

20. The end effector according to claim 15, further comprising a jaw aperture stop disposed on one of the first or second jaw members and configured to limit movement of the first and second jaw members relative to one another.

* * * * *